(12) United States Patent
Park et al.

(10) Patent No.: US 9,081,012 B2
(45) Date of Patent: Jul. 14, 2015

(54) METHOD FOR DIAGNOSING A DISEASE USING EXTRACELLULAR VESICLES COMPRISING POROUS POLYMER MONOLITH MICROFILTER

(71) Applicant: POSTECH ACADEMY-INDUSTRY FOUNDATION, Pohang-si, Gyeongsangbuk-do (KR)

(72) Inventors: Jae Sung Park, Pohang-si (KR); Jun Ho Kim, Pohang-si (KR); Ryan Thomas Davies, Pohang-si (KR)

(73) Assignee: POSTECH ACADEMY-INDUSTRY FOUNDATION, Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 13/826,485

(22) Filed: Mar. 14, 2013

(65) Prior Publication Data
US 2014/0113295 A1 Apr. 24, 2014

(30) Foreign Application Priority Data

Oct. 19, 2012 (KR) .......... 10-2012-0116926

(51) Int. Cl.
 C12Q 1/68 (2006.01)
 C12P 19/34 (2006.01)
 G01N 33/574 (2006.01)
 B01L 3/00 (2006.01)
 G01N 1/40 (2006.01)

(52) U.S. Cl.
 CPC .............. *G01N 33/574* (2013.01); *C12P 19/34* (2013.01); *C12Q 1/68* (2013.01); *B01L 3/502753* (2013.01); *G01N 2001/4088* (2013.01)

(58) Field of Classification Search
 CPC .................................. C12Q 1/68; C12P 19/34
 USPC ................................... 435/6.1, 91.2
 See application file for complete search history.

(56) References Cited

U.S. PATENT DOCUMENTS 8,414,754 B1 * 4/2013 Santiago et al. ............. 204/549
2013/0178383 A1 * 7/2013 Spetzler et al. ................. 506/9

OTHER PUBLICATIONS

R.T. Davies, et al; Microfluidic filtration system to isolate extracellular vesicles from blood; Lab on a Chip; 2012; vol. 12; pp. 5202-5210.
Korean Office Action dated Mar. 21, 2014.
Ryan Davies, et al., Microfluidic Crossflow Filtration System to Isolate Extracellular Vesicles From Blood, 2012 ISEV Annual Scientific Meetinc, Apr. 2012.
Jaesung Park, et al., Epigenetic Reprogramming and Diagnosis by Micromachining Technology, Multisclae BioMechanical Engineering Laboratory, 2012.
Ryan Davies, et al., Microfluidic Crossflow Filtration System to Isolate Extracellular Vesicles From Blood, 2012 ISEV Annual Scientific Meeting, Oct. 2012.

* cited by examiner

*Primary Examiner* — Ardin Marschel
(74) *Attorney, Agent, or Firm* — Lucas & Mercanti, LLP

(57) ABSTRACT

The present invention relates to an apparatus for the isolation of extracellular vesicles from human fluid, and more particularly, to an apparatus comprising a channel formed on a microchip and a porous polymer monolith filter connected to the channel. The apparatus can be used to the diagnosis of disease including cancer from vesicular nucleic acid in a non-invasive manner. Capable of isolating and purifying a large quantity of vesicles from a small amount of a body fluid sample within a short time, the apparatus is expected to be advantageously and widely applied in the medical research and clinical diagnosis of disease including cancer.

12 Claims, 14 Drawing Sheets

Fig. 12

| Sample | Average RNA amount (ng) / protein (100 μg) |
|---|---|
| Pressure driven | 6.62 (± 1.84) |
| Electro. driven | 79.10 (± 67.31) |
| Ultra. EV | 186.81 (± 27.23) |

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Melan A forward primer

<400> SEQUENCE: 1
cgctcctatg tcactgctga                                               20

<210> SEQ ID NO 2
<211> LENGTH: 20
<212> TYPE: DNA
<213> ORGANISM: Artificial Sequence
<220> FEATURE:
<223> OTHER INFORMATION: Melan A reverse primer

<400> SEQUENCE: 2
ggtgatcagg gctctcacat                                               20

<210> SEQ ID NO 3
<211> LENGTH: 18
<212> TYPE: DNA
<213> ORGANISM: Artificial Sequence
<220> FEATURE:
<223> OTHER INFORMATION: beta actin forward primer

<400> SEQUENCE: 3
gagggaaatc gtgcgtga                                                 18

<210> SEQ ID NO 4
<211> LENGTH: 19
<212> TYPE: DNA
<213> ORGANISM: Artificial Sequence
<220> FEATURE:
<223> OTHER INFORMATION: beta actin reverse primer

<400> SEQUENCE: 4
ccaagaagga aggctggaa                                                19

1

METHOD FOR DIAGNOSING A DISEASE USING EXTRACELLULAR VESICLES COMPRISING POROUS POLYMER MONOLITH MICROFILTER

FIELD OF THE INVENTION

The present invention relates to an apparatus for the isolation of extracellular vesicles from human fluid, and more particularly, to an apparatus comprising a channel formed on a microchip and a porous polymer monolith filter connected to the channel.

BACKGROUND OF THE INVENTION

When diagnosed early, most cancers are more apt to be prevented from metastasizing, which gives rise to a higher survival rate for patients. However, high diversity of cancer-related factors contributes to the difficulty of early diagnosis. Active studies have been directed towards biomarkers that are available for the early diagnosis of cancer. One of the most interesting biomarkers is cancer cell RNA. For use in diagnosis, the RNA has been obtained from cancer cells separated from excised cancer tissues or from CTC (circulating tumor cells) in the bloodstream. However, the excision is accompanied by an operation that is invasive to the subject, and the finding of CTC is poor in effectiveness because it is too rare, e.g., one cells per $10^9$ blood cells, to detect.

Most cells shed extracellular vesicles (EV) into body fluid. EV serves as a transporter carrying various materials including proteins, lipids, amino acids, etc. These substances have recently been revealed to be important factors that are indicative of properties of the EV sources, that is, the cells shedding the EV. Thus, newly increasing recognition has been given to the importance of EV. Particularly, cancer cells shed a number of vesicles containing metastasis factors. Cancer cell-shed vesicles are present at a higher level in blood and thus are easier to apply to the diagnosis of cancer, compared to CTC. The vesicles shed from cancer cells can, therefore, be used for early diagnosis of cancer in a non-invasive manner.

In addition to the small size of vesicles, micron-sized substances and blood cells other than vesicles makes it difficult to obtain information on cancer cells from vesicles. For example, the extraction of information about vesicular nucleic acids of cancer cells by performing PCR (polymerase chain reaction), a powerful tool of analyzing nucleic acids, such as RNA, is obstructed by DNAs of blood cells such as leucocytes, and by pigments of hemoglobin. It is predicted that information derived from vesicles, if isolated with the exclusion of these obstacles, would be useful in the early diagnosis of cancer.

However, no effective and accurate methods of isolating vesicles from body fluid have been developed, thus far. Centrifugation is representative of the isolation methods of vesicles developed thus far. Primarily, cells are, for example, separated from body fluid on the basis of density difference using a centrifugal separator. Then, centrifugation at higher speeds removes other microparticles and aqueous solutions. However, the centrifugation method is operated in multiple steps, requiring much labor. In addition, the method needs huge facilities as well as a large quantity of body fluid, and thus it is impossible to apply to practical diagnosis in which only a small amount of samples can be utilized. In addition, it takes at least 4 hours to complete the centrifugation method, so that it is not suitable for clinical diagnosis requiring rapidity. A method for isolating microvesicles from body fluid using a microchip onto which an antibody to vesicular proteins is immobilized was developed (US 20120142001 of Skog et al., entitled "Method for isolation of nucleic acid containing particles and extraction of nucleic acids therefrom"), by which vesicles can be isolated within a short time. However, this method requires a centrifugation procedure for cell removal. A method that is capable of isolating vesicles from a small quantity of body fluid without using complex facilities such as centrifugation separators or without requiring the immobilization of antibodies to collection channels is advantageous in application to clinical diagnosis.

Leading to the present invention, intensive and thorough research into the isolation of vesicles has resulted in developing a microfilter system that is capable of effectively isolating microvesicles in a non-invasive manner and in finding that the microfilter system is applicable to the clinical diagnosis of cancer.

SUMMARY OF THE INVENTION

Accordingly, the present invention has been made keeping in mind the above problems occurring in the prior art, and objects of the present invention are to provide an apparatus for the isolation of extracellular vesicles from body fluid, comprising a porous polymer monolith filter, a method for the fabrication thereof, and a method for diagnosing a disease using the same. However, it should be noted that the objects to be achieved by the present invention are not limited to the foregoing objects and that other non-mentioned objects could be apparently understood from the following descriptions by those skilled in the art.

BRIEF DESCRIPTION OF THE DRAWINGS

The above and other objects, features and other advantages of the present invention will be more clearly understood from the following detailed description taken in conjunction with the accompanying drawings, in which:

FIG. 12 is a table showing relative RNA contents to protein in vesicles separated from respective modes, wherein numerals in parentheses are error ranges of six measurements;

DETAILED DESCRIPTION OF THE INVENTION

Figure 1:
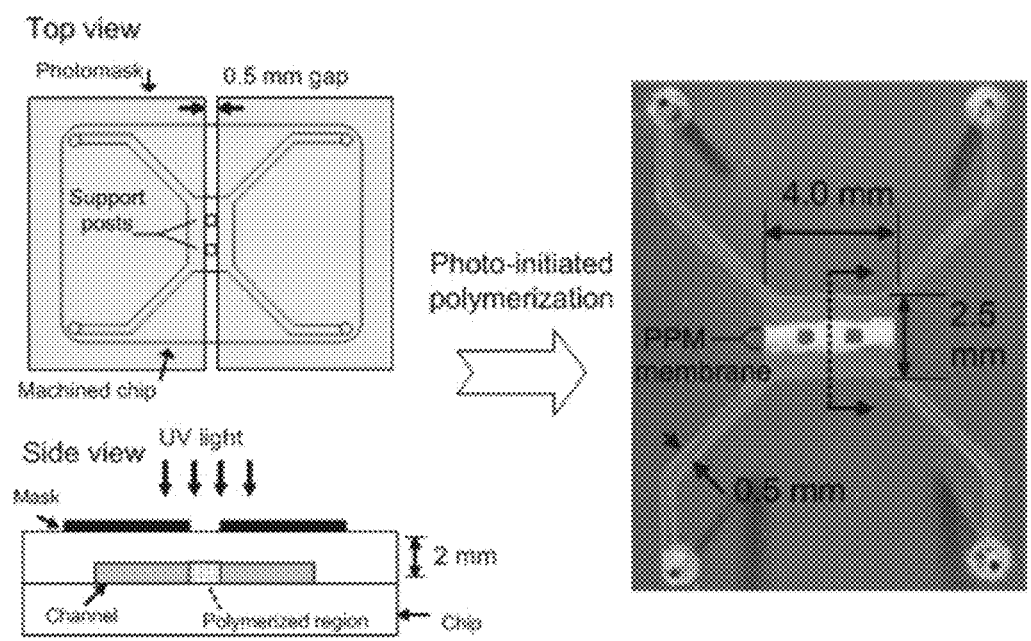
FIG. 1 shows a process of the fabrication of a PPM filter system in which a channel carved in a cross flow pattern on a microchip is filled with a PPM prepolymer solution and only a central region is exposed to UV to form a PPM filter.

In accordance with an aspect thereof, the present invention provides an apparatus for the isolation of extracellular vesicles from body fluid, comprising:
 a channel, formed on a microchip, for flowing a fluid therethrough; and
 a porous polymer monolith filter connected to the channel.

In one embodiment of the present invention, the microchip is made of a material selected from the group consisting of polymethyl methacrylate, cyclic olefin copolymer, polycarbonate, polystyrene, and polydimethylsiloxane. Although a microchip made of polymethyl methacrylate is given in the Example section, thermoplastic polymers such as cyclic olefin copolymers, and other polystyrene resins may be used to make a microchip, but materials of the microchip are not limited thereto.

In another embodiment of the present invention, the channel has a structure in which two channel are formed in a cross pattern. On a microchip, two channels are formed in a cross form with a PPM (porous polymer monolith) filter located at the intersection of the cross flow channels. However, the configuration of the channels and the number of PPM filters may be varied, and are not limited to the embodiment. For instance, the microchip structure may be fabricated by connecting only one channel, but not cross flow channels, to a PPM filter.

In a further embodiment of the present invention, two or more PPM filters are arranged in sequence. In this regard, the PPM filters may be identical to or different from each other in terms of pore size. To isolate microvesicles in a stepwise manner, the PPM filters may be arranged so that body fluid passes through the filters in a decreasing order of pore sizes. However, the number and arrangement of the filters are not limited to the embodiment.

In still another embodiment of the present invention, glycidyl methacrylate or an antibody to a specific vesicular protein is immobilized to the surface of the channel. When coated with glycidyl methacrylate, the surface of the channel is negatively charged, functioning to prevent negatively charged vesicles from adsorbing onto the channel before passing through the filter. On the other hand, antibodies to CD9, CD63 or CD81, markers expressed on vesicles, when attached to a specific site of the channel, allow the fixation of vesicles on that site, which can be applied to the detection experiment such as PCR and ELISA.

In a still further embodiment of the present invention, the apparatus utilizes a pressure and/or electric field as a driving force to flow fluid through the channel. The pressure may be produced by a pump. The pressure and the electric field that are used as driving forces for the filtration may be varied in a controlled manner. In the following Example section, apparatuses utilizing a pressure and an electric field as respective driving forces were fabricated, separately. A pressure and an electric field may be used together as driving forces for isolating vesicles in the apparatus of the present invention. For example, vesicles and small protein mass may be separated together using pressure, and then separated from each other by a filter under an electric filed. As a driving force, a pressure has the advantage of separating many vesicles, while filtration under an electric field allows the isolation of relatively pure vesicles from impurities such as proteins.

In yet another embodiment of the present invention, the vesicles are derived from cancer cells. Cancer cells are known to shed a large quantity of vesicles. However, the origin of vesicles is not limited to cancer cells. The vesicles from cells other than cancer cells can be used to the diagnosis using the apparatus of this invention. Although melanoma cells are exemplified below, cells of other diseases such as leukemia, if releasing vesicles, can be a target of diagnosis.

In a yet further embodiment of the present invention, the porous polymer monolith filter ranges in pore size from 100 nm to 5 μm. Although vesicles with a diameter of 500 nm or less are illustrated below, the pore size may be adjusted so that vesicles of different sizes can be separated.

In accordance with another aspect thereof, the present invention provides a method for fabricating an apparatus for the isolation of extracellular vesicles, comprising:
 A) forming a channel and a groove connected the channel;
 B) injecting a porous polymer monolith prepolymer solution into the groove through the channel; and C) polymerizing the porous polymer monolith prepolymer solution at the groove with UV light.

In one embodiment of the present invention, the PPM prepolymer solution of step B) comprises a porogenic solvent in an amount of from 58% to 68% by weight based on the total weight of the solution. However, the content of the porogenic solvent is not limited to the amounts. Since a PPM prepolymer solution with a higher content of the porogenic solvent results in a PPM filter with a larger pore size, the content of the porogenic solvent may be controlled according to the sizes of the vesicles to be isolated.

In accordance with a further aspect thereof, the present invention provides a method for diagnosing a disease, using the apparatus of claim 1, comprising:

A) isolating extracellular vesicles from body fluid using the apparatus of claim 1; and B) analyzing a nucleic acid prepared from the extracellular vesicles.

In one embodiment of the present invention, the body fluid may be whole blood, a serum, peritoneal fluid, milk or urine, but is not limited thereto. Although blood taken from mice is illustrated in the following Example section, body fluid from humans, non-human primates, rats, dogs, cats, horses and cows may be used as a source of vesicles in the apparatus of the present invention. The origin of body fluid is not limited to the above-mentioned animals.

In another embodiment of the present invention, the disease is cancer.

A better understanding of the present invention may be obtained through the following examples which are set forth to illustrate, but are not to be construed as limiting, the present invention.

EXAMPLES

Example 1 is set forth as illustrating a method for fabricating the apparatus of the present invention.

Example 2 is set forth as determining the pore size of a PPM filter used in the apparatus of the present invention.

In Examples 3 and 4, a pressure and an electric field are used as a driving force for operating the apparatus of the present invention, respectively.

In Examples 5 to 7, the apparatus of the present invention is examined for capacity and performance concerning the amount and purity of the detected vesicles in terms of hemolysis, DNA content and vesicular morphology, respectively.

Example 8 is set forth as illustrating the application of the apparatus of the present invention to the diagnosis of cancer.

Example 1

Fabrication of PMMA (Polymethyl Methacrylate) Microchannel Associated with PPM (Porous Polymer Monolith) Filter 1-1. Formation of PMMA Microchannel Microchannels were fabricated using PMMA as a base material. PMMA is suitable as a material for channel formation because it has high durability and is easy to pattern, is permeable to UV light and is compatible with other material.

Using a MICO CNC (TinyCNC-S, TinyRobo, Korea), crossflow channel with a depth of 150 μm and a width of 500 μm was carved in the form of X-shape on a PMMA plate, while a rectangular groove for a PPM filter was formed with dimensions of 2.5×4.0 mm at the intersection of the crossflow channels. The PMMA plate on which the channels and the groove were formed was washed with 100% ethanol before a cover plate was attached to the PMMA plate using 5 μl of methyl methacrylate (purchased from Aldrich) and fixed in an oven (1 hr, 65° C.) Afterwards, 23-gauge steel hypodermic needle segments were connected to the ends of the channels at the four corners of the PMMA plate and fixed in an oven (2 hrs, 65° C.)

1-2. Preparation of PPM Filter Prepolymer Solution

A PPM prepolymer solution was prepared by mixing 1.8 mL of glycidyl methacrylate (GMA) monomer, 1.3 mL of ethylene glycol dimethacrylate (EGDMA), 40 mg of 2,2-dimethoxy-2-phenyl-acetophenone (DMPA), 10 mg of hydroquinone, and 4.3-6.6 mL of methanol (58% to 68% of total volume). All of the materials were purchased from Aldrich. To deoxygenate the solution, it was purged for 2 min with nitrogen gas.

In the solution, glycidyl methacrylate serves as a reaction initiator and makes the surface of the channel negatively charged, thereby preventing the adsorption of negatively charged vesicles into the channel. In addition, this monomer has an acryl group chemically similar to PMMA, functioning to mediate the firm fixation of the monolith into the channel surface after polymerization. Ethylene glycol dimethacrylate was used as a cross-linker, 2,2-dimethoxy-2-phenyl-acetophenone was used as a photo-initiator, and methanol was used as a porogenic solvent. Hydroquinone served as a polymerization initiator which played a role in preventing the non-specific polymerization attributable to the transmission of heat or the diffusion of polymerization during UV-initiated polymerization.

1-3. Fabrication of PPM Filter

The channel plate patterned in 1-1 was covered with a shadow mask designed to limit the width of a central site where a PPM filter is to be formed (left upper and lower panels of FIG. 1) to 0.5 mm. Thereafter, the needle segments at the four corners of the channel plate were connected with a flexible plastic Tygon tube (Norton Performance Plastics, USA) (i.d. 0.508 mm) through which the PPM prepolymer solution prepared in 1-2 was then infused. Next, the tube was tied to block the introduction of oxygen, followed by exposure to UV light at 365 nm from a UV light source (SUV 2010-S, UV Sources & Manufacturing Technology, Korea) (17 min). After completion of the polymerization, ethanol and water were sequentially allowed to flow to remove the unreacted solution. The completed channel was used immediately or stored with water introduced thereinto (the light panel of FIG. 1).

Figure 2:
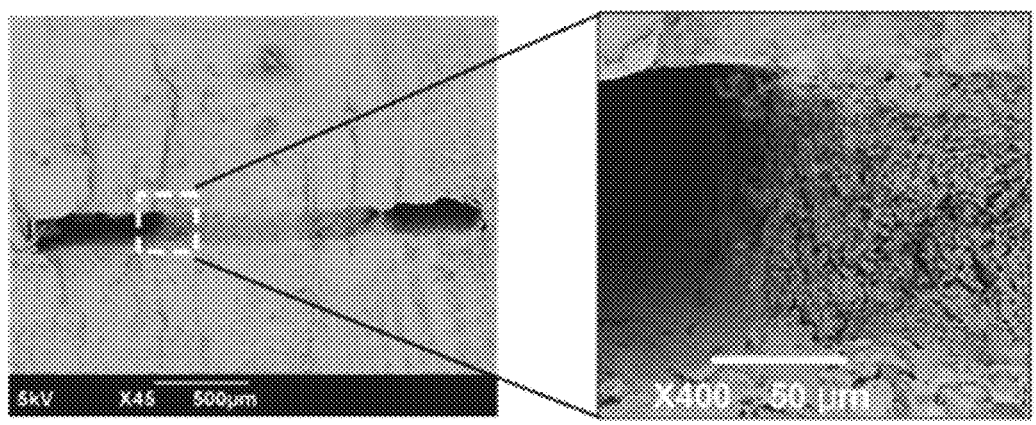
FIG. 2 shows SEM images of a conjunction between the PPM filter and the channel.

FIG. 2 shows a clear boundary between the fabricated filter and the channel lumen.

Example 2

Porosity of PPM Filter

The porosity of the PPM filter varies depending on the composition of the PPM prepolymer solution, and particularly the content of the porogenic solvent is known to have direct influences on the porosity of the filter. A PPM filter becomes porous as monolith beads are formed in a net structure.

In order to determine the porosity of the filter fabricated in Example 1, fluorescent polystryrene beads of various sizes were passed through the filter. Because the filter did not pass beads larger than the pore size thereof, the pore size was determined by that of the fluorescent polystyrene beads (Duke Scientific) filtrated into the collection channel (FIG. 4a).

Figure 3:
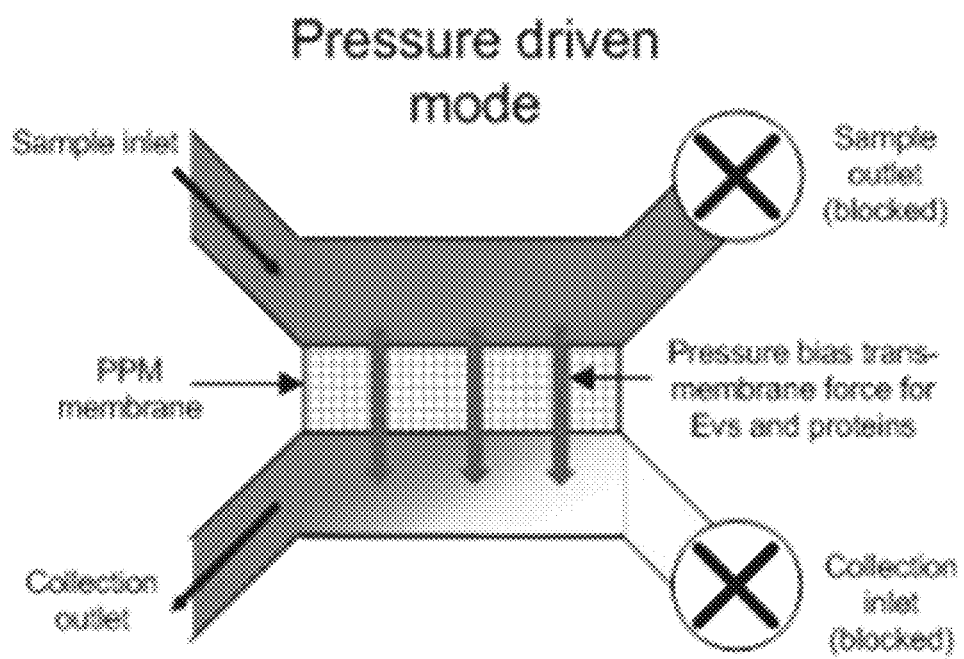
FIG. 3 is a diagram showing a flow path of fluid in a pressure-driven PPM filter system, with vesicles and proteins separated from each other by the PPM filter, wherein the symbol X represents the temporary blockage of one end of each channel path.

FIG. 3 is a schematic diagram of a channel system operating in a pressure-driven mode in accordance with the present invention, with inlet and outlet of each sample and collection designated. In the context of determining the porosity, a syringe pump was connected to the inlet of the sample channel (where a sample would be introduced), and fluorescent polystyrene beads of various sizes were introduced into the sample channel to remove gas therefrom, after which the sample outlet was blocked. Separately, 1×PBS (phosphate buffer saline) was introduced into the collection channel (where filtrates passing the PPM filter would be collected) to remove gas therefrom, after which the collection inlet was blocked. In this condition, fluid was forced to flow at a rate of 1.0 μl/min using the pump (Harvard Apparatus). As a result, filtrates passing through the PPM were collected in the collection channel due to a pressure difference. PBS was infused in an amount of 18.5 μl corresponding to the total volume of one channel to evacuate the filtrates from the channel.

Figure 4:
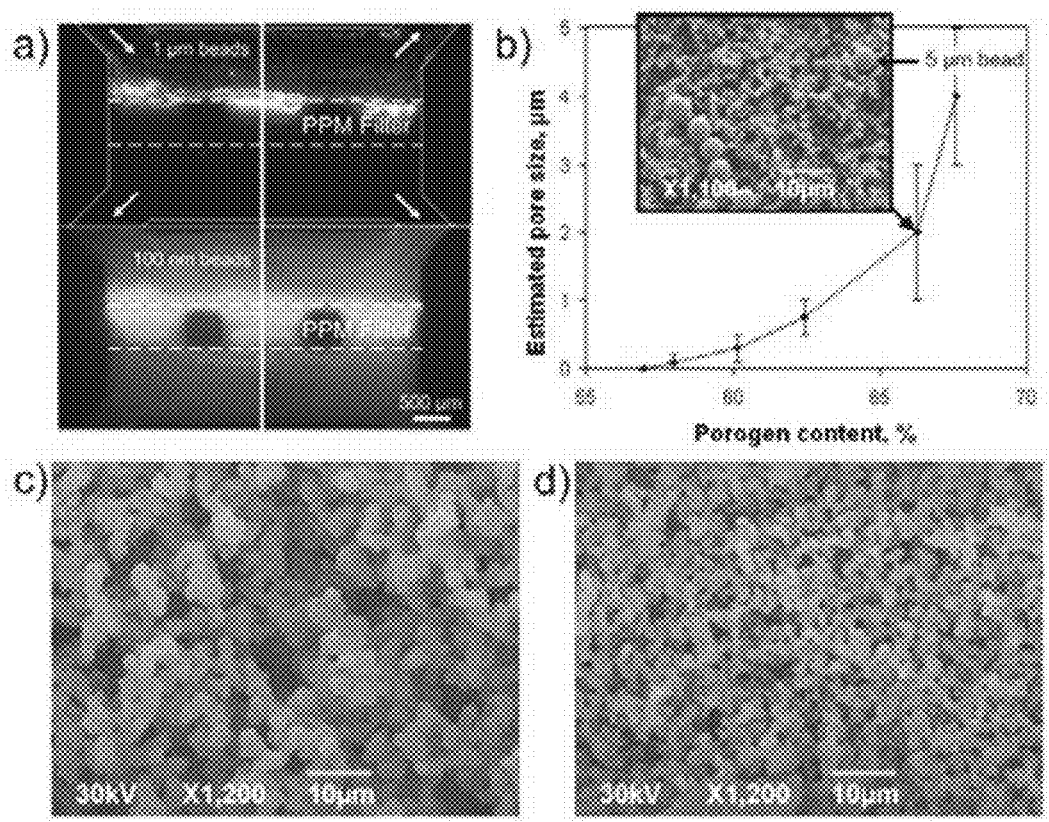
FIG. 4a shows the filtering capacity of a PPM filter prepared from a PPM prepolymer solution with a porogenic solvent content of 60% in which red fluorescent beads with a size of 1 µm are entrapped by the filter (upper panel) whereas green beads with a size of 100 nm pass through the filter (lower panel)
FIG. 4b is a graph in which estimated pore sizes are plotted against porogenic solvent contents, with an SEM image insert showing the entrapment of 5-µm polystyrene beads by the filter prepared from a PPM prepolymer solution with a porogenic solvent content of 66%.
FIG. 4c is a photographic image showing the formation of large pores in a PPM filter prepared from a solution with a porogenic solvent content of 67%.
FIG. 4d is a photographic image showing the formation of small pores in a PPM filter prepared from a solution with a porogenic solvent content of 58%.

When the PPM prepolymer solution contained a porogenic solvent in an amount of 57% or less by weight based on the total weight of the solution, the PPM filter was observed to have a pore size of 100 nm or less, whereas a porogenic solvent content of 70% or higher allowed for a pore size of 5 μm or greater (FIGS. 4c and 4d).

FIG. 4b is a graph illustrating that when the content of a porogenic solvent in a PPM prepolymer solution is decreased, smaller monolith beads are produced with the consequent formation of smaller pore sizes. The insert in FIG. 4b is a photograph showing that beads with a diameter of 5 μm cannot pass through the filter prepared from a solution with a porogenic solvent content of 66%.

Example 3

Isolation of Vesicles through PPM Filter System—Pressure-Driven Mode

FIG. 3 is a schematic diagram of a channel system operating in a pressure-driven mode in accordance with the present invention. Vesicles were isolated from blood using this system.

3-1. Isolation of Vesicles by PPM Filter System

A syringe pump was connected to the inlet of the sample channel (where a sample would be introduced), and fluorescent polystyrene beads of various sizes were introduced into the sample channel to remove gas therefrom, after which the sample outlet was blocked. Separately, 1×PBS (phosphate buffered saline) was introduced into the collection channel (where filtrates passing the PPM filter would be collected) to remove gas therefrom, after which the collection inlet was blocked. In this condition, fluid was forced to flow at a rate of 1.0 μl/min using the pump (Harvard Apparatus). As a result, filtrates passing through the PPM were collected in the collection channel due to a pressure difference. PBS was infused in an amount of 18.5 μl corresponding to the total volume of one channel to evacuate the filtrates from the channel. After completion of the evacuation for 40 min, the extract amounted to about 4 μl.

Figure 5:
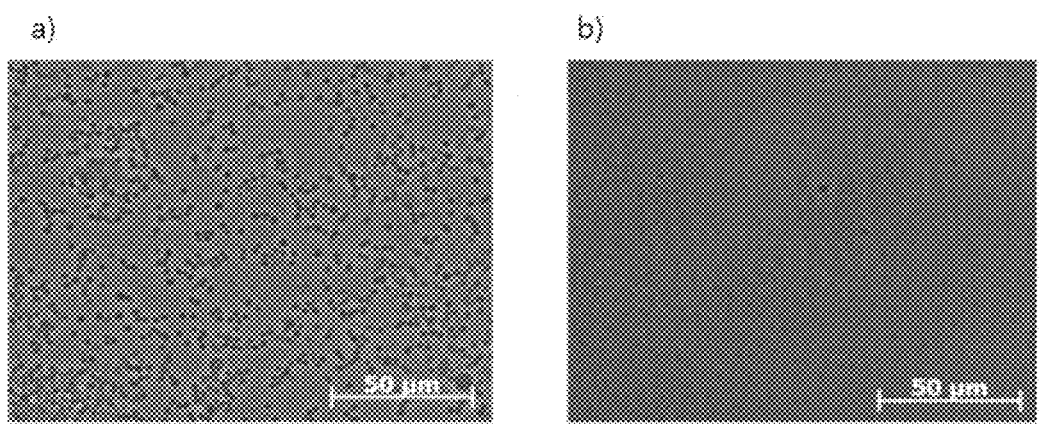
FIG. 5a is a photographic image of blood cells before passing through a filter.
FIG. 5b is a photographic image of the blood fluid after passing through the PPM filter in a pressure-driven mode, showing that cells are removed from blood.

In this regard, the PPM filter functioned in a passive mode so that it removed only matter greater than 500 nm in size (white and red blood cells). When blood was forced to pass through the PPM filter, as can be seen in FIG. 5, extracellular vesicles and other sub-cellular particles were separated. In the right panel of FIG. 5, vesicles were observed to remain intact without undergoing aggregation and destruction.

3-2. Determination of Pore Size of Filter

To determine the filter pore size suitable for use in isolating extracellular vesicles from blood, body fluid was flowed through channels against filters with various pore sizes. Because filters with smaller pore sizes were apt to be blocked within a shorter time, the time taken to clog the filter was employed as a parameter.

Figure 6:
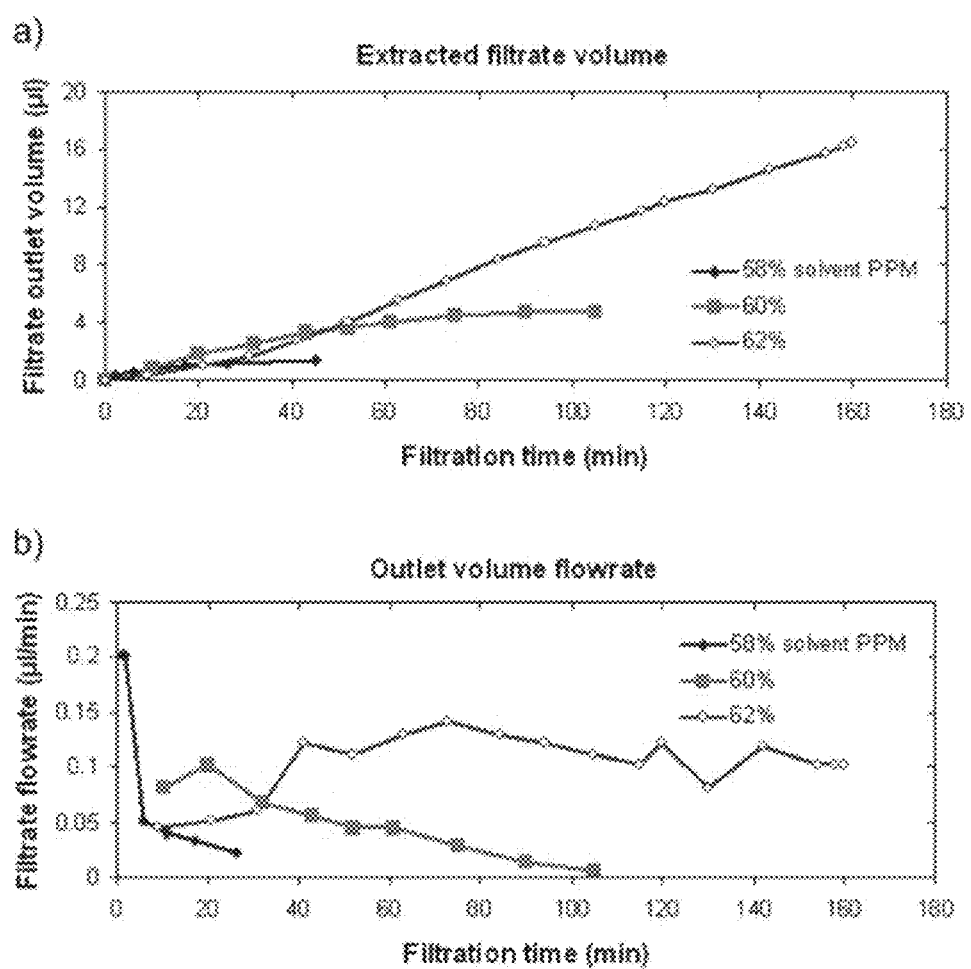
FIG. 6a is a graph in which cumulated volumes of the filtered fluid are plotted against filtration time according to porogenic solvent contents.
FIG. 6b is a graph showing the passage rates of fluid through the filters against filtration time.

Times taken for the filters to be clogged at a pumping rate of 1.0 μl/min, were compared. No additional increase in volume was regarded as clogging of the filters. The volumes of the filtrate emerging from the outlet were plotted against time in FIG. 6a, while the flow rates of filtrate calculated over time were given in FIG. 6b. Fluid was allowed to pass through a filter (pore size 100 nm) polymerized from a PPM prepolymer solution with a porogenic solvent content of 58%, a filter (pore size 500 nm) polymerized from a PPM prepolymer solution with a porogenic solvent content of 60%, and a filter (pore size 1 μm) polymerized from a PPM prepolymer solution with a porogenic solvent content of 68%, and the results are represented with blue, red and violet lines respectively. The filters with large pore sizes (>500 mm, polymerized from a solution with a porogenic solvent content >60%) allowed fluid to pass therethrough irrespective of flow rates, but some red points were also observed, indicating the passage of cells (red blood cells). On the other hand, filters with small pore sizes were clogged by various cells. The filter polymerized from a solution with a porogenic solvent content of 60% was found to pass a sufficient amount of fluid therethrough before it was clogged. The volume of the filtrate amounted to about 4 μl, which was considered sufficient to perform PCR analysis or other diagnosis methods therewith because 10 nl of a sample typically suffices for the operation of PCR. Therefore, the filtrate was predicted to isolate an amount of target matter sufficient to be applied to PCR and other various diagnosis apparatuses.

Example 4

Isolation of Vesicles Through PPM Filter System—Electro-Driven Mode

Cells and cell-derived vesicles are negatively charged due to phospholipids. The negative charges of proteins and other substances are typically less intense than those of extracellular vesicles. This phenomenon was applied to the PPM filter system as follows.

4-1. Identification of Negative Charge of Vesicles

Vesicles and serum proteins (BAS) separated from blood by ultracentrifugation were found to have a zeta potential of −19.30 mV (+/−0.08) and −13.20 mV (+/−0.06) at pH 7.5, respectively, as measured by DLS (Zetasizer 3000HSA, Malvern). Because zeta potential is directly related with mobility in an electric field, the results imply the high likelihood that vesicles would be superior to proteins in motility.

Figure 7:
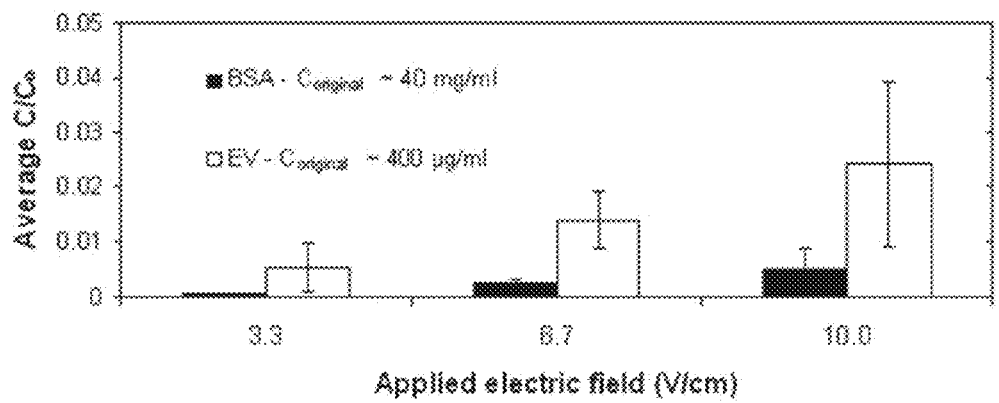
FIG. 7 is a graph showing the effect of an electric field as a driving force on the filtration of the protein BSA (bovine serum albumin) and vesicles in an electro-driven PPM filter system, in which the motility of each test sample is calculated by dividing the concentration of the filtrate by the concentration of the introduced sample.

To confirm the results, the motility was measured in the presence of electric fields. Each bovine serum albumin (40 mg/ml) and extracellular vesicles (400 g/ml) in 1×TAE buffers were respectively exposed to an electric field of 3.3-10 V/cm applied across the PPM filter. As can be seen in FIG. 7, BSA and extracellular vesicles were isolated in different amounts at the same voltage. In all of the tested electric fields, extracellular vesicles were extracted in larger amounts than BSA. When the electric field was higher than 6.7 V/cm, a lot of bubbles were formed around the electrodes to interfere with the flow of the fluid, causing greater measurement errors. Hence, the electric field was set to 6.7 V/cm or less.

4-2. Electro-Driven PPM Filter System

On the basis of the result obtained in the experiment of 4-1, a PPM filter system for isolating extracellular vesicles from abundant blood proteins and cells was constructed.

Figure 8:
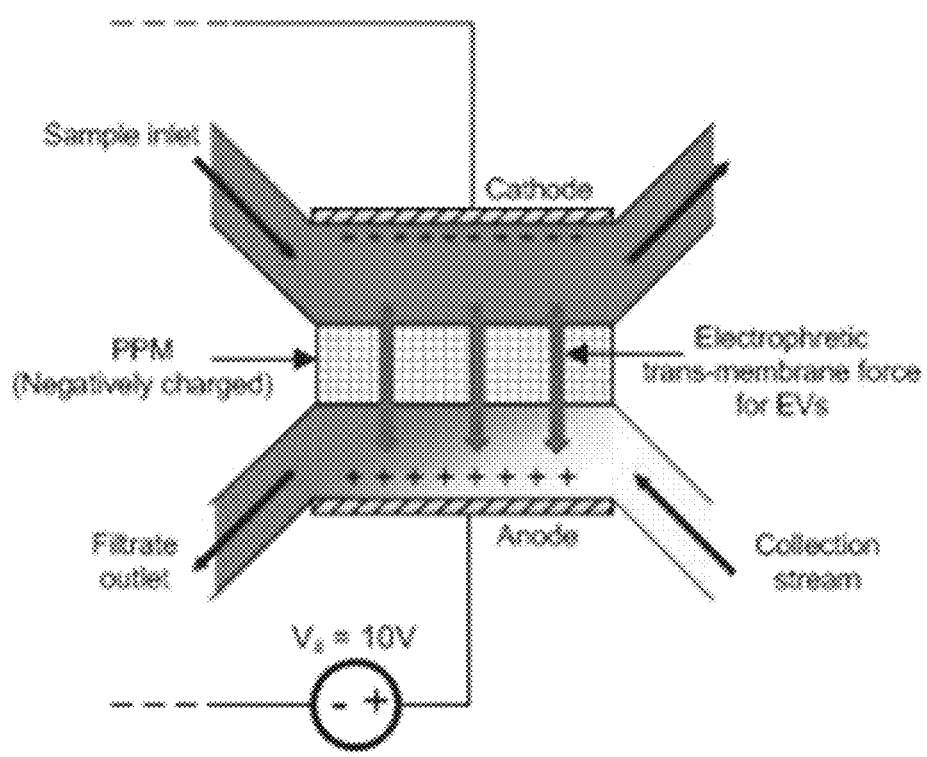
FIG. 8 is a schematic diagram of an electro-driven PPM filter system showing flow directions of fluid, and the passage of vesicles and proteins through the filter, with an electric field of 6.7 V/cm generated across the filter by applying a voltage of 10 V between two electrodes 1.5 cm apart from each other.

25×TAE was mixed at a ratio of 1:24 with blood to give a blood solution in 1×TAE, which was then subjected to direct current electrophoresis. Fluid was continuously run at a rate of 2 μl/min through both of the channels in a crossflow form. Using a DC power supply (DRP-1001, Digital Electronics Co. Ltd., Korea), an electric potential of 10 V (an electric field of 6.25 V/cm) was applied between the two opposite channels through which blood and the filtrate were run, respectively, with iron needles connected to the power supply and the channels. This system is schematically diagramed in FIG. 8. About 240 μl of blood was fed for 2 hrs. Like the pressure-driven PPM filter system of Example 3, the electro-driven PPM filter system did not suffer from any clogging problem.

Example 5

Efficacy of Isolation Method—Hemolysis and DNA Content

To examine the efficacy of the pressure-driven PPM filter system and the electro-driven PPM filter system respectively fabricated in Examples 3 and 4, a measurement was made of hemolysis of red blood cells and DNA contents. Hemolysis is a general parameter indicative of the damage of blood cells while a DNA content is a parameter for force exerting on cells because DNA is released as a result of cell lysis. When white blood cells were lysed, DNA was highly apt to exist in the filtrate if filtration was operated irrespective of sizes. When red blood cells were disrupted, hemoglobin was released, causing discoloration.

5-1. Hemolysis

Figure 9:
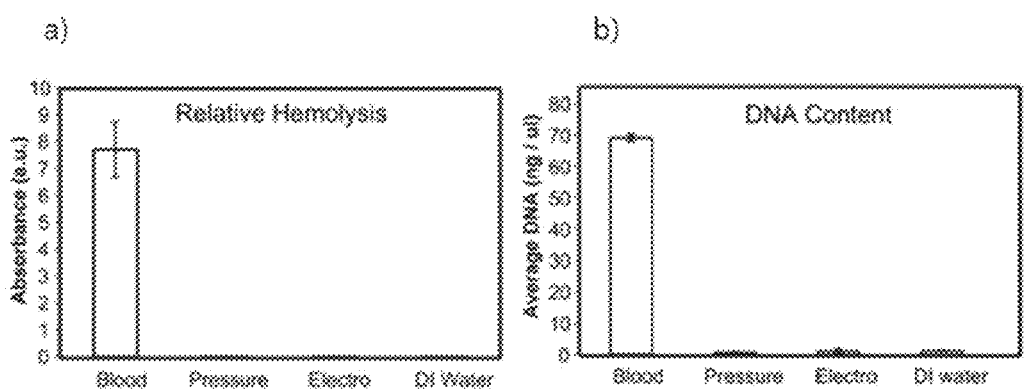
FIG. 9a is a graph showing that both the pressure- and the electro-driven PPM filter system cause negligible hemolysis as compared to 40-fold diluted blood (2.5% hemolysis)
FIG. 9b is a graph showing that the content of cellular DNA in the filtrate using the pressure- or the electro-driven PPM filter system is too negligible to measure.

Mouse blood was applied to the pressure- or electro-drive PPM filter system. Assuming that a 40-fold dilution of blood in water exhibits 2.5% hemolysis, samples collected from each system were examined for hemolysis without dilution. As seen in FIG. 9a, both of the samples passing through the pressure- or the electro-driven system experienced little hemolysis, compared to 2.5% hemolysis, indicating that almost no red blood cells were disrupted.

5-2. DNA Content

To examine the presence or absence of cellular DNA in the vesicle solution eluted from the PPM filter, the solution was subjected to lysis (lysis buffer [50 mM Tris (pH 8.0), 100 mM EDTA, 100 mM NaCl, 1% SDS, 250 μg/ml protease K], 90 min, 60° C.). Then, 3 M of potassium acetate was mixed at a ratio of 1:3 with the lyzed sample, followed by centrifugation at 13,500 g for 10 min. The supernatant was added with 0.3 mL of chloroform, and centrifuged (13,500 g, 10 min). The pellet thus formed was mixed with 100% ethanol and centrifuged again (13,500 g, 10 min). The pellet was dissolved in 20 μl of deionized (DI) water to give a DNA solution.

DNA levels were determined using a spectrophotometer (Nanodrop SD2000, BioPrince). The samples were found to have DNA at a concentration of 0.76 (+/−0.10) ng/ml after extraction through the pressure-driven PPM filter system, and at a concentration of 1.08 (+/−0.78) ng/ml after extraction through the electro-driven PPM filter system. In consideration of the absorbance (0.56+/−0.10 ng/ml) of DI water, DNA was observed to be almost absent in both of the samples emerging from the PPM filter systems (FIG. 9b).

Example 6

Influence of Electric Field—Hemolysis

The pressure-driven filter system may be apt to disrupt cells and vesicles by pressure. As a driving force, an electric field, although known to have a smaller influence on cells and vesicles than pressure, may cause perforation or disruption by heat or electricity.

Theoretically, the damage of direct current on cells may be represented by $|Vtm|=1.5|E|R$, wherein Vtm, E, and R are a membrane potential, an electric field, and a radius of material, respectively. Given an electric field of 6.7 V/cm, a cell with a diameter of 1 μm is found to have a membrane potential of 0.5 mV. A smaller membrane potential is generated in vesicles which are smaller than cells. According to previous reports that cells are disrupted and perforated at 1 V and 0.25V, respectively, it is predicted that cellular substance would be little apt to be present in the solution of vesicles emerging from the PPM filter system of the present invention.

When blood passed through the filter, a pH change might have influences on blood cells or vesicles, for example, might disrupt cells or vesicles. To monitor pH changes, the following experiment was conducted.

Before application to the PPM filter system, mouse blood was measured to have a pH of 7.0. After filtration through the PPM filter system, the mouse blood sample was subjected to electrophoresis for 2 hrs and then measured to have a pH of 7.5. This small pH change indicates that blood does not generally experience a significant change during filtration through the PPM filter system of the present invention.

Example 7

Comparison of Properties of Isolated Vesicles

Properties of the vesicles isolated using the pressure-driven PPM filter system, the electro-drive filter system, and a conventional ultracentrifugation method were compared as follows.

7-1 Isolation of Vesicles

A pressure-driven PPM filter system and an electro-drive filter system were constructed as in Examples 3 and 4, respectively. Extracellular vesicles were isolated from mouse blood through these systems.

Ultracentrifugational isolation was conducted as follows. Blood taken from a mouse heart was treated with 5 mM EDTA and centrifuged at 800×g for 10 min. The supernatant was diluted in 9 volumes of PBS (EDTA 5 mM) and centrifuged again at 3,000×g for 20 min. After ultracentrifugation at 100,000×g for 2 hrs, the pellet thus formed was diluted in PBS. As much proteins as possible were removed by re-ultracentrifugation at 100,000×g for 2 hrs.

7-2 Quantitative and Morphological Comparison of Isolated Vesicles

Figure 10:
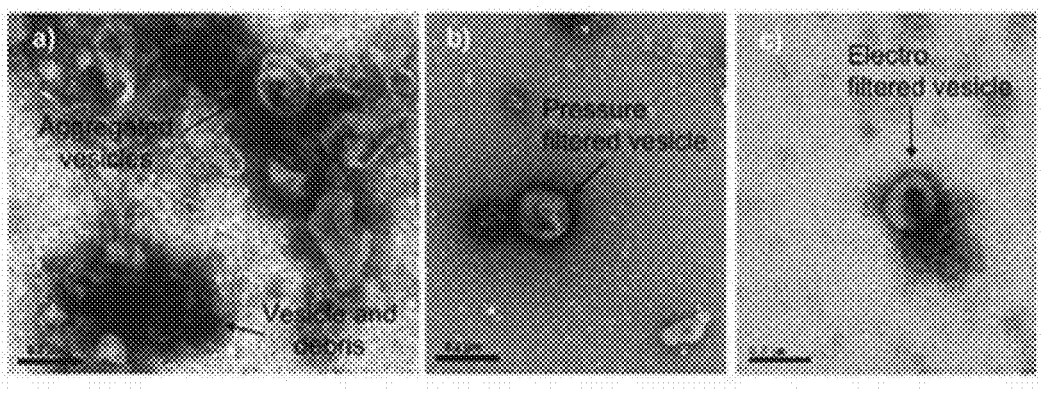
FIG. 10 shows TEM images of vesicles obtained by ultracentifugation (A), a pressure-driven filter system (B), and an electro-driven filter system (C).

Vesicles were observed using TEM (transmission electron microscopy). FIG. 10a is a TEM image of the samples isolated by ultracentrifugation, showing that many vesicles were isolated, but they were aggregated, and partially underwent a morphological change by disruption. FIG. 10b is a TEM image of a sample emerging from the pressure-driven PPM filter system. As can be seen, although the sample was smaller in the amount of vesicle than that isolated by ultracentrifugation and had a small amount of proteins, the vesicles remained intact with a diameter of 150 nm. FIG. 10c is a TEM image of the sample emerging from the electro-driven PPM filter system, showing a similar result to that of FIG. 10b.

7-3 Quantitative Comparison of Proteins Specific for Vesicles

The level of CD9, a protein specific for vesicles, in a sample may indirectly represent the purity of the isolated vesicles. In this regard, the following experiment was carried out.

Using each of the three methods described in 7-1, vesicles were isolated from 25 μl of blood. The filtrate was mixed at a ratio of 10:1 with TCA (trichloroacetic acid solution, Aldrich) (6.1 N) to precipitate all proteins and vesicles. Following centrifugation for 10 min at 13,500×g, the resulting pellet was mixed with one volume of electrophoresis loading buffer (50 mM Tris-HCl/2% SDS/0.1% bromophenol blue/10% glycerol) and boiled at 100° C. for 10 min to denature proteins. The resulting sample was divided equally, and loaded into a test well and a control well of 12% resolving gel. Proteins were separated by size using SDS PAGE (120 V, 1.5 hrs), and transferred onto a PVDF membrane at 390 mA for 2 hrs (4° C.). For the test group, a 0.1 μg/ml CD9 primary antibody (BD Biosciences, NA/LE Rat Anti-Mouse) was diluted in a blocking solution (0.3% BSA/0.1% tween20/TBS) while only a blocking solution was used in the control group.

Figure 11:
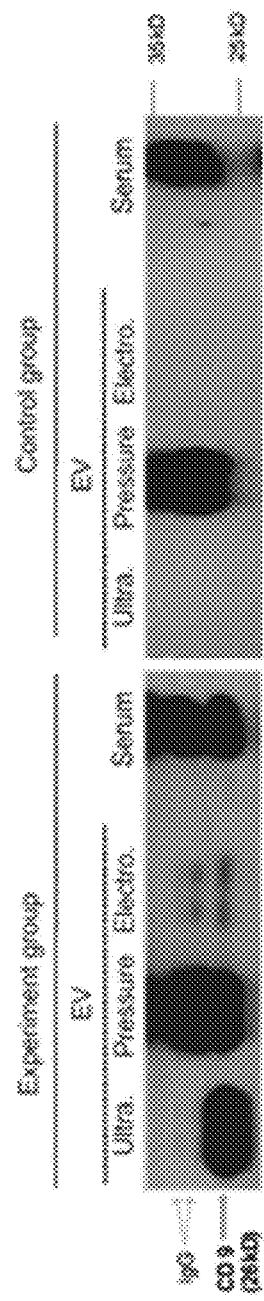
FIG. 11 shows immunoblot images of an experiment group (treated with a primary and a secondary antibody) (left panel) and a control group (treated only with a secondary antibody) wherein, of the three bands visualized in the left panel, two came from IgG present in blood and the other one accounted for the quantity of CD9 expressed in vesicles, and wherein two IgG bands are only visualized in the right panel, demonstrating that the bands in other position of the experimental group represents CD9 protein.

The sample emerging from the pressure-driven PPM filter system was observed to contain CD9 and other serum proteins in large quantities. On the other hand, the filtrate sample obtained from the electro-driven PPM filter system, although less in CD9 level compared to the pressure-driven PPM filter system, contained CD9 in a much large quantity than other serum proteins (FIG. 11). That is, when isolated in an electric field, the vesicles were improved in purity whereas more vesicles were isolated using a pressure. Thus, the pressure-driven PPM filter system and the electro-driven PPM filter system are advantageous quantitatively and qualitatively, respectively.

7-4. Comparison of RNA Level

Since free RNA in blood has a very short half-life due to circulating RNase, the RNA found in the filtrate sample may probably originate from vesicles. Thus, the performance of the filter can be indirectly examined by comparing the levels of protein and RNA in the sample emerging from the filter system. In this regard, the following experiment was carried out.

Using each of the three methods described in 7-1, vesicles were isolated. The filtrate was incubated with 0.8 mL of Tryzol (Life Technologies) for 5 min to dissolve the vesicle membrane. The addition of 0.2 mL of chloroform separated RNA from other materials (proteins and DNA) (5 min, 4° C.). Distinct layers were formed by centrifugation at 13,500×g for 10 min, and the supernatant (RNA layer) was mixed with one volume of IPA (isopropyl alcohol) to precipitate RNA (20 min, −20° C.). Following re-centrifugation at 13,500×g for 10 min, the pellet was washed with 75% ethanol. This was centrifuged again at 13,500×g for 10 min to form an RNA precipitate. Ethanol was aspirated, and the resultant pellet was dried at room temperature for 5 min or longer and diluted in DI water. The concentration of the RNA solution was determined using a spectrophotometer (Nanodrop SD2000, BioPrince).

When a pressure was used as a driving force, a large quantity of RNA was obtained, but together with a large quantity of proteins, indicating low purity of vesicles. On the other hand, when using an electric field as a driving force, the PPM filter system allowed for a higher content of RNA than proteins, like ultracentrifugation. These results were coincident with those obtained in Example 7-3. Therefore, the pressure-driven PPM filter system and the electro-driven filter system could be construed to have quantitative and qualitative advantages, respectively. Also, the data show that an electrokinetic function is effective for selectively removing proteins from complex fluids such as blood.

Example 8

Diagnosis Using Isolated Vesicles

Melan A, although expressed in normal cells, is used as a diagnosis marker for melanoma because it is abundantly found in melanoma tumor cells. To examine whether isolated vesicles can be applied to diagnosis, a measurement was made of the presence of melan A in the filtrate obtained from the blood of mice which had been implanted with the cancer cells.

B16BL6 (mouse melanoma tumor cells) were subcutaneously injected at a dose of $2 \times 10^6$ cells into a side region of 6-week-old mice (C57BL6/j mice) and grown for three weeks. Thereafter, blood was taken from the heart, and added with 5 mM EDTA to prevent coagulation before application to vesicle isolation. For control, blood was taken from normal mice which had not been transplanted with cancer cells.

Using a pump, the blood samples were fed at a flow rate of 1.0 μl/min into the pressure-driven PPM filter system until the channel was clogged.

To the electro-driven PPM filter system, a solution in which 25×TAE was mixed at a ratio of 1:24 with the blood sample was applied, followed by direct current electrophoresis.

Fluid was continuously run at a rate of 2 μl/min through both of the channels to prevent the channels from being clogged. Using a DC power supply (DRP-1001, Digital Electronics Co. Ltd., Korea), an electric potential of 10 V (an electric field of 6.25 V/cm) was applied between the two opposite channels through which blood and the filtrate were run, respectively, with iron needles connected to both the power supply and the channels.

For use in vesicle isolation by ultracentrifugation, blood taken from the mouse heart was treated with 5 mM EDTA and centrifuged at 800×g for 10 min. The supernatant was diluted in 9 volumes of PBS (EDTA 5 mM) and centrifuged again at 3,000×g for 20 min. After ultracentrifugation at 100,000×g for 2 hrs, the pellet thus formed was diluted in PBS. As much proteins as possible were removed by re-ultracentrifugation at 100,000×g for 2 hrs.

Using each of the three methods described in 7-1, vesicles were isolated from 25 μl of blood. The filtrate was incubated with 0.8 mL of Tryzol (Life Technologies) for 5 min to dissolve the vesicle membrane. The addition of 0.2 mL of chloroform separated RNA from other materials (proteins and DNA) (5 min, 4° C.). Distinct layers were formed by centrifugation at 13,500×g for 10 min, and the supernatant (RNA layer) was mixed with one volume of IPA (isopropyl alcohol) to precipitate RNA (20 min, −20° C.). Following re-centrifugation at 13,500×g for 10 min, the pellet was washed with 75% ethanol. This was centrifuged again at 13,500×g for 10 min to form an RNA precipitate. Ethanol was aspirated, and the pellet was dried at room temperature for 5 min or longer and diluted in DI water. The concentration of the RNA solution was determined using a spectrophotometer (Nanodrop SD2000, BioPrince). Visualization was achieved with ETBR (ethidium bromide) dye. To compare the quantity of RNA with the positive control (embryonic stem cells), the housekeeping gene actin RNA was employed.

RT-PCR was performed with the isolated RNA. From the RNA, cDNA was synthesized in the presence of poly A primer using a reverse transcription kit (Promega, GoScript). A gene of interest was amplified from the cDNA transcript using primers therefor, with the aid of a polymerase chain reaction kit (Promega, GoTaq). The PCR product was isolated by electrophoresis on 1.5% agarose gel for 30 min at 120 V. In the context of the detection of Melan A, the forward and the reverse primer were designed to have the sequences of 5'-CGCTCCTATGTCACTGCTGA-3' (SEQ ID NO: 1) and 5'-GGTGATCAGGGCTCTCACAT-3' (SEQ ID NO: 2), respectively while 5'-GAGGGAAATCGTGCGTGA-3' (SEQ ID NO: 3) and 5'-CCAAGAAGGAAGGCTGGAA-3' (SEQ ID NO: 4) were set forth as a forward and a reverse primer for the housekeeping gene β-actin. PCR started with denaturation at 90° C. for 5 min, and was run with 30 cycles of denaturation at 90° C. for 30 sec, annealing at 50° C. for 30 sec, and elongation at 72° C. for 30 sec, followed by final elongation at 72° C. for 10 min.

Figure 13:
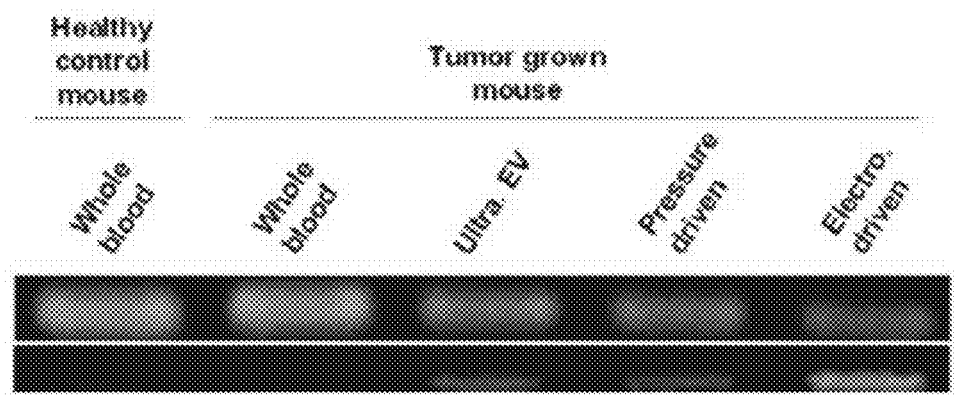
FIG. 13 is a photograph of PCR products that were obtained from vesicles separated in respective modes wherein a band of the housekeeping gene β-actin (upper) is constantly visualized for all groups, whereas a band of the cancer marker melan A (lower) is shown only on the lanes of the vesicles obtained by ultracentrifugation or the filter systems.
Figure 14:
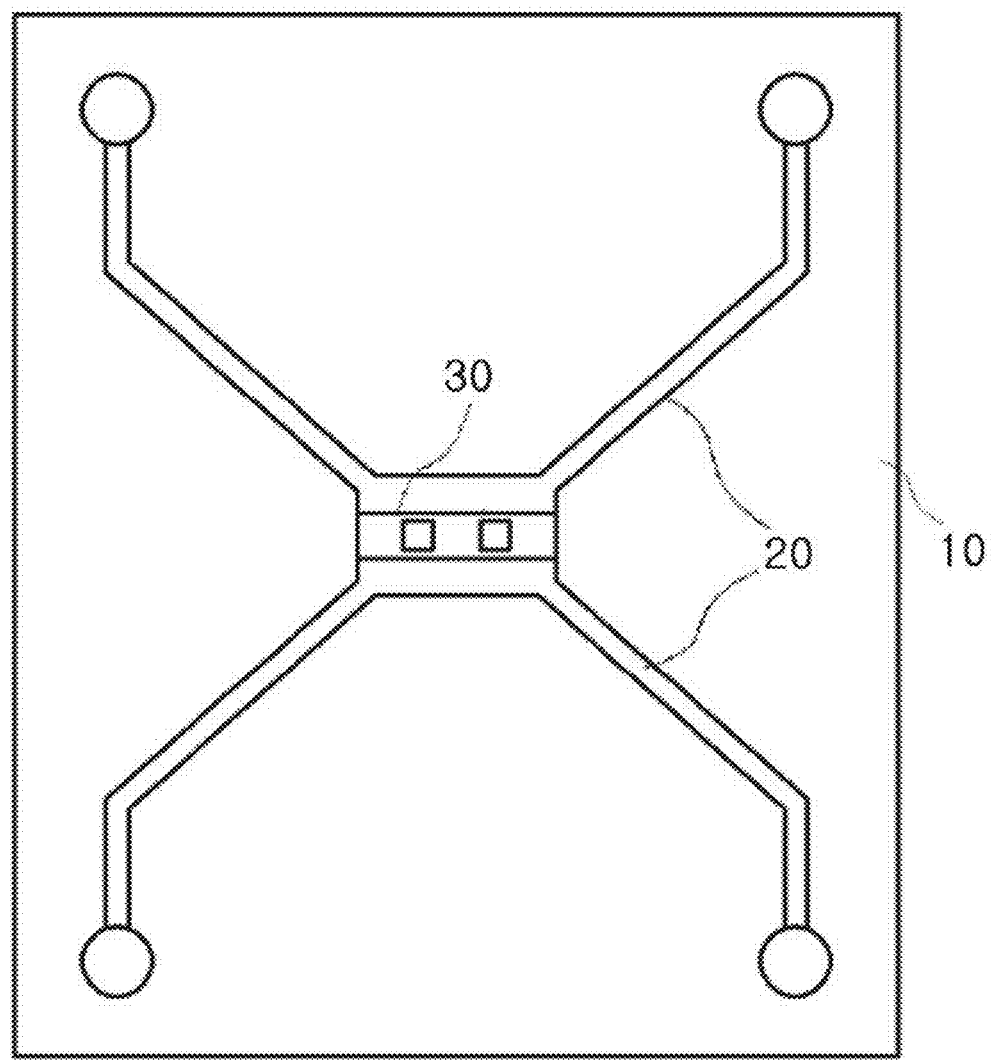
FIG. 14 is a schematic diagram of an apparatus according to one embodiment of the present invention, wherein a microchip is represented by numeral 10, a channel by numeral 20, and a PPM filter by numeral 30.

As can be seen in FIG. 13, a melan A band was shown from both of the filtrates emerging from the pressure-driven PPM filter system and the electro-driven PPM filter system. The same band was observed when the ultracentrifugation method was used. However, almost no melan A bands were detected from the control blood containing various proteins and cells. Therefore, the pressure- or electro-driven PPM filter system of the present invention can isolate the cancer-related genes on the same level as in the ultracentrifugation method, and can be applied, in combination with PCR, to the diagnosis of cancer.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. The teachings of the invention provided herein can be applied to other systems. These and other changes can be made to the invention in light of the detailed description As described above, the apparatus of the present invention may be used to the diagnosis of diseases including cancer from vesicular nucleic acid in a non-invasive manner. Capable of isolating and purifying a large quantity of vesicles from a small amount of a body fluid sample within a short time, the apparatus of the present invention is expected to be advantageously and widely applied in the medical research and clinical diagnosis of diseases including cancer.

What is claimed is:

1. A method for diagnosing a disease, using an apparatus for isolation of extracellular vesicles from body fluid, comprising:
   A) isolating extracellular vesicles from body fluid using the apparatus;
   B) extracting a nucleic acid from the extracellular vesicles obtained from step (A);
   C) performing polymerase chain reaction (PCR) on the nucleic acid obtained from step (B); and
   D) diagnosing a disease by analyzing the PCR product, wherein
   the apparatus comprises a channel formed on a microchip for flowing a fluid therethrough; and
   a porous polymer monolith filter;
      wherein the porous polymer monolith (PPM) filter is formed by polymerizing a porous polymer monolith prepolymer in the channel.

2. The method of claim 1, wherein the body fluid is selected from the group consisting of whole blood, a serum, peritoneal fluid, breast milk, and urine.

3. The method of claim 1, wherein the disease is cancer.

4. The method of claim 1, wherein the microchip is made of a material selected from the group consisting of polymethyl methacrylate, cyclic olefin copolymer, polycarbonate, polystyrene, and polydimethylsiloxane.

5. The method of claim 1, wherein the channel has a structure in which two channels are formed in a cross pattern.

6. The method of claim 1, wherein the porous polymer monolith filter comprises two or more filter units, said filter units being arranged in sequence.

7. The method of claim 6, wherein the filter units of the porous polymer monolith filter are different from one to another in pore size.

8. The method of claim 1, further comprising a generator of a driving force by which fluid is allowed to flow through the channel, said generator being selected from the group consisting of a pressure generator, an electric field generator, and a combination thereof.

9. The method of claim 1, wherein the extracellular vesicles originate from cancer cells.

10. The method of claim 1, wherein the porous polymer monolith filter ranges in pore size from 100 nm to 5 μm.

11. The method of claim 1, wherein the porous polymer monolith filter is formed by injecting a solution of the porous polymer monolith prepolymer into the channel, polymerizing the porous polymer monolith prepolymer, and ejecting an unreacted portion of the porous polymer monolith prepolymer solution from the channel.

12. The method of claim 1, wherein the apparatus further comprising a generator of a driving force by which fluid is allowed to flow through the channel, wherein the generator is an electric field generator.

* * * * *